(12) United States Patent
Rush (10) Patent No.: US 7,662,617 B2
(45) Date of Patent: Feb. 16, 2010

(54) SYSTEMS AND PROCESSES FOR CELLULOSIC ETHANOL PRODUCTION

(76) Inventor: Stephen L. Rush, P.O. Box 543, San Bernardino, CA (US) 92410

( * ) Notice: Subject to any disclaimer, the term of this patent is extended or adjusted under 35 U.S.C. 154(b) by 0 days.

(21) Appl. No.: 12/419,891

(22) Filed: Apr. 7, 2009

(65) Prior Publication Data

US 2009/0181440 A1 Jul. 16, 2009

Related U.S. Application Data (63) Continuation-in-part of application No. 12/192,815, filed on Aug. 15, 2008, now Pat. No. 7,514,247, which is a continuation-in-part of application No. 12/014,090, filed on Jan. 14, 2008, now Pat. No. 7,449,313, which is a continuation-in-part of application No. 11/934,768, filed on Nov. 3, 2007, now abandoned.

(51) Int. Cl.
| | |
|---|---|
| C12M 1/00 | (2006.01) |
| C12M 1/02 | (2006.01) |
| C12M 1/06 | (2006.01) |
| C12M 1/113 | (2006.01) |
| C12P 7/06 | (2006.01) |
| C12N 1/00 | (2006.01) |
| C12N 1/12 | (2006.01) |
| C12N 1/18 | (2006.01) |
| C12P 1/04 | (2006.01) |
| C12P 1/02 | (2006.01) |

(52) U.S. Cl. ............ 435/289.1; 435/161; 435/135; 435/170; 435/171; 435/195; 435/243; 435/254.2; 435/257.1

(58) Field of Classification Search ............ 435/135, 435/161, 170, 171, 195, 243, 254.2, 257.1, 435/289.1
See application file for complete search history.

(56) References Cited

U.S. PATENT DOCUMENTS

| 4,275,167 A | 6/1981 | Wicklow et al. |
|---|---|---|
| 4,321,327 A | 3/1982 | Chen et al. |
| 4,427,775 A | 1/1984 | Chen et al. |
| 4,840,903 A | 6/1989 | Wu |
| 5,677,154 A | 10/1997 | Van Draanen et al. |
| 5,932,456 A | 8/1999 | Van Draanen et al. |
| 6,846,657 B2 | 1/2005 | Heikkila et al. |
| 7,109,005 B2 | 9/2006 | Eroma et al. |
| 2003/0180900 A1 | 9/2003 | Lantero |
| 2004/0231060 A1 | 11/2004 | Burdette et al. |
| 2005/0170483 A1 | 8/2005 | Elnashaie et al. |
| 2006/0014260 A1 | 1/2006 | Fan et al. |
| 2006/0177917 A1 | 8/2006 | Warzywoda et al. |
| 2006/0246563 A1 | 11/2006 | Eroma et al. |
| 2006/0275882 A1 | 12/2006 | Martinez-Gutierrez et al. |
| 2007/0048848 A1 | 3/2007 | Sears |
| 2007/0178569 A1 | 8/2007 | Leschine et al. |
| 2007/0202583 A1 | 8/2007 | Smith et al. |
| 2007/0231869 A1 | 10/2007 | Holmgren et al. |
| 2008/0028675 A1 | 2/2008 | Clifford, III et al. |
| 2008/0044877 A1 | 2/2008 | Penttila et al. |
| 2008/0057555 A1 | 3/2008 | Nguyen |
| 2008/0085341 A1 | 4/2008 | Dai et al. |
| 2008/0102503 A1 | 5/2008 | Rush |
| 2008/0241902 A1* | 10/2008 | Berry et al. ............ 435/161 |

FOREIGN PATENT DOCUMENTS

| CN | 1880415 | 12/2006 |
|---|---|---|
| CN | 1912129 | 2/2007 |
| DE | 212533 | 8/1984 |
| DE | 19921561 | 11/2000 |
| JP | 58036392 | 3/1983 |
| JP | 61224995 | 10/1986 |
| RU | 2037001 C1 | 6/1995 |
| WO | WO 2006096130 | 9/2006 |
| WO | WO 2006100667 | 9/2006 |
| WO | WO 2007025145 | 3/2007 |
| WO | WO200791231 | 8/2007 |
| WO | WO 2009/029344 A1 * | 3/2009 |

OTHER PUBLICATIONS

Balan, V, Da Costa Sousa L., Chundawat SP, Vismeh R, Jones AD, Dale BE, "Mushroom Spent Straw: A Potential Substrate for an Ethanol-Based Biorefinery", Journal of Ind. Microbiol. Biotechnology, Jan. 8, 2008.

Kuyper, et al, "High-level functional expression of a fungal xylose isomerase: the key to efficient ethanolic fermentation of xylose by *Saccharomyces cerevisiae?*", FEMS Yeast Research vol. 4, pp. 69-78, Jan. 9, 2006.

(Continued)

*Primary Examiner*—Jon P Weber
*Assistant Examiner*—Kailash C Srivastava
(74) *Attorney, Agent, or Firm*—Booth Udall, PLC (57) ABSTRACT

A cellulosic ethanol production system. Implementations may include a feed stage that may produce a raw cellulose stream from a waste cellulose stream and an algae cellulose stream. A hydrolysis stage may produce a hydrolyzed cellulose stream. A liquefaction stage may produce a formed sugars stream and one or more liquefaction byproduct streams. A fermentation stage may react the formed sugars stream with a yeast feed in at least one fermenter to produce a raw ethanol stream. A separation stage may separate ethanol from the raw ethanol stream and to produce a fuel ethanol stream. An algae generation stage may include at least one algae bioreactor and may react the one or more liquefaction byproduct streams with algae in the at least one algae bioreactor to produce an algae stream. A biodiesel production stage may produce a biodiesel stream and the algae cellulose stream.

4 Claims, 3 Drawing Sheets

OTHER PUBLICATIONS

Schirmer-Michel, Angela Cristina, et al., "Production of ethanol from soybean hull hydrolysate by osmotolerant *Candida guilliermondii* NRRL Y-2075", Bioresource Technology 99, pp. 2898-2904, May 2008.

Katahira S. et al, "Ethanol fermentation from lignocellulosic hydrolysate by a recombinant xylose- and cellooligosaccharide-assimilating yeast strain", Applied Microbiology and Biotechnology, vol. 72/6, pp. 1136-1143, Oct. 1, 2006.

Karhumaa K. et al., "Co-utilization of L-arabinose and D-xylose by laboratory and industrial *Saccharomyces cerevisiae* strains", Microbial Cell Factories, Apr. 10, 2006.

Jeffries T.W. et al., "Metabolic engineering for improved fermentation of pentoses by yeasts", Applied Microbiology and Biotechnology, vol. 63/5, pp. 495-509, Feb. 1, 2004.

Leathers T.D. et al., "Bioconversions of maize residues to value-added coproducts using yeast-like fungi", FEMS Yeast Research, vol. 3/2, pp. 133-140, Apr. 1, 2003.

Holmgren M. et al., "Identification of white-rot and soft-rot fungi increasing ethanol production from spent sulfite liquor in co-culture with *Saccharomyces cerevisiae*", Journal of Applied Microbiology, vol. 105, pp. 134-140, Jul. 2008.

Pandey, A., "Concise encyclopedia of bioresource technology", Food Products Press Binghamton, USA, 2004.

Roca C. et al., "Increasing ethanol productivity during xylose fermentation by cell recycling of recombinant *Saccharomyces cerevisiae* biofuel production by yeast having xylose-reductase and xylitoldehydrogenase activity", Applied Microbiology and Biotechnology, vol. 60, Issue 5, pp. 560-563, 2003.

Steenbakkers et al., "b-Glucosidase in cellulosome of the anaerobic fungus *Piromyces* sp. strain E2 is a family 3 glycoside hydrolase", Biochem. J., vol. 370, pp. 963-970, 2003.

Mckenna, Phil, "From Smokestack to Gas Tank," New Scientist, vol. 191, issue 2572.

Bauchop, et al., "Cellulose Fermentation by a Rumen Anaerobic Fungus in Both the Absence and the Presence of Rumen Methanogens," Appl. and Environ. Microbiology, p. 1103-1110, vol. 42, No. 6 (Dec. 1981).

Dijkerman, et al., "Cultivation of Anaerobic Fungi in a 10-1 Fermenter System For the Production of (hemi-) cellulolytic Enzymes," Appl. Microbiol. Biotechnol., p. 85-91, vol. 46 (1996).

Sreenath, et al., "Production of Ethanol From Wood Hydrolyzate By Yeasts," Bioresource Technology, p. 253-260, vol. 72 (2000).

Derzko, et al., "Smart Economy," available at http://smarteconomy.typepad.com/2006/10/algae_bioreacto.html (2006).

Nigam, JN, "Ethanol production from hardwood spent sulfite liquor using an adapted strain of *Pichia stipitis*", Journal of Industrial Microbiology & Biotechnology, vol. 26, pp. 145-150 (2001).

* cited by examiner

SYSTEMS AND PROCESSES FOR CELLULOSIC ETHANOL PRODUCTION

CROSS REFERENCE TO RELATED APPLICATIONS

This application is a continuation-in-part application of the earlier U.S. Utility patent application to Stephen LeRoy Rush entitled "Systems and Processes for Cellulosic Ethanol Production," application Ser. No. 12/192,815, filed Aug. 15, 2008, now U.S. Pat. No. 7,514,247, issued Apr. 7, 2009, which was a continuation-in-part application of the earlier U.S. Utility patent application to Stephen LeRoy Rush entitled "Systems and Processes for Cellulosic Ethanol Production," application Ser. No. 12/014,090, filed Jan. 14, 2008, now U.S. Pat. No. 7,449,313, issued Nov. 11, 2008, which was a continuation-in-part application of the earlier U.S. Utility patent application to Stephen LeRoy Rush entitled "Process For The Organic Breakdown of Cellulosic Tissue," application Ser. No. 11/934,768, filed Nov. 3, 2007, now abandoned, the disclosures of which are hereby incorporated entirely herein by reference.

BACKGROUND

1. Technical Field

Aspects of this document relate generally to processes and systems for fuel production from biomass sources.

2. Background Art

The derivation of fuels from biomass sources has been in long practice. For example, ethanol and biodiesel derived from biomass sources are becoming increasingly adopted as fuel sources in internal combustion engines. Conventional ethanol generation technology involves processing a starchy source material (such as a grain or vegetable) by converting the starch source to free glucose and fermenting the glucose with yeast that excretes significant amounts of ethanol. Conventional biodiesel generation technology involves processing a feedstock, such as vegetable oil, through a reaction process such as transesterification to produce biodiesel and a variety of other byproducts. Other processes have been developed to generate a variety of other fuel-related materials from biomass, including lubricants, fuel additives, and greases.

An example of a conventional ethanol production process may be found in U.S. Pat. No. 4,885,241, to Millichip entitled "Ethanol production by *Zymomonas* cultured in yeast-conditioned media," issued Dec. 5, 1989, the contents of which are hereby incorporated entirely herein by reference.

An example of a conventional biodiesel generating process may be found in U.S. Pat. No. 5,713,965 to Foglia, et al., entitled "Production of biodiesel, lubricants and fuel and lubricant additives," issued Feb. 3, 1998, the contents of which are hereby incorporated entirely herein by reference.

SUMMARY

Implementations of cellulosic ethanol production systems may include first implementations of integrated cellulosic ethanol and biodiesel production systems. Implementations may include a feed stage configured to receive a waste cellulose stream and an algae cellulose stream and to produce a raw cellulose stream and a hydrolysis stage coupled with the feed stage and configured to hydrolyze the raw cellulose stream to produce a hydrolyzed cellulose stream. The system may also include a liquefaction stage coupled with the hydrolysis stage and configured to liquefy the hydrolyzed cellulose stream to produce a formed sugars stream and one or more liquefaction byproduct streams. The system may include a fermentation stage coupled with the liquefaction stage and configured to react the formed sugars stream with a yeast feed in at least one fermenter to produce a raw ethanol stream, a separation stage that may be coupled with the fermentation stage and configured to separate ethanol from the raw ethanol stream and to produce a fuel ethanol stream, and an algae generation stage including at least one algae bioreactor and configured to react the one or more liquefaction byproduct streams with algae in the at least one algae bioreactor to produce an algae stream. The system may include a biodiesel production stage coupled with the algae generation stage and configured to produce a biodiesel stream and the algae cellulose stream.

Implementations of first implementations of integrated cellulosic ethanol and biodiesel production systems may include one, all, or any of the following:

The system may include one or more hydrolysis inputs and the one or more hydrolysis inputs may include one or more compounds configured to reduce the concentration of auxin in the raw cellulose stream, assist in dehydrogenation of the raw cellulose stream, modify the pH of the raw cellulose stream, or any combination thereof.

The one or more compounds may be one of capsaicin, quercetin, genestine, ethanol, and any combination thereof.

The one or more compounds may be one or more enzymes selected from the group consisting of dehydrogenase, formate, alcohol dehydrogenase E, cytosol, excrements of cephalopods or ocean mammals, and any combination thereof.

The one or more liquefaction byproduct streams may include xylitol.

Implementations of cellulosic ethanol production systems may include second implementations of integrated cellulosic ethanol and biodiesel production systems. Implementations may include a feed stage having a feed operation having a grinding operation and a mixing operation. The grinding operation may be configured to produce a waste cellulose stream and the mixing operation may be configured to receive the waste cellulose stream and an algae stream and to produce a raw cellulose stream. The system may also include a hydrolysis stage coupled to the feed stage having a hydrolysis operation configured to react the raw cellulose stream with one or more organisms included in one or more hydrolysis inputs to produce a hydrolyzed cellulose stream, a hydrolysis $CO_2$ stream, and a hydrolysis ethanol stream. The system may also include a liquefaction stage coupled with the hydrolysis stage that includes a heated sugar formation operation, a organisms separation operation, and a liquefaction operation. The heated sugar formation operation and the liquefaction operation may be configured to liquefy the hydrolyzed cellulose stream to produce a sugars stream and the organisms separation operation may be configured to produce a recycled organism stream. The system may include a sugars separation stage coupled with the liquefaction stage that includes a sugar separation operation configured to produce a xylitol stream and a separated sugars stream from the sugars stream. A fermentation stage may be coupled with the sugars separation stage and may include a fermentation operation configured to react the separated sugars stream with a yeast feed in at least one fermenter to produce a raw ethanol stream and a fermentation $CO_2$ stream. A separation stage may be coupled with the fermentation stage and may include a separation operation configured to separate ethanol from the raw ethanol stream to produce a fuel ethanol stream and a waste cellulose stream. An algae generation stage including an algae generation operation may be included, the algae generation operation having at least one algae bioreactor. The algae generation operation may be configured to react the hydrolysis $CO_2$ stream, the fermentation $CO_2$ stream, an atmospheric $CO_2$ stream, and the xylitol stream with algae in the at least one algae bioreactor to produce an algae stream. A biodiesel production stage may be coupled with the algae generation stage and may include a biodiesel reaction operation and an algae drying operation. The biodiesel reaction operation may be configured to produce a biodiesel stream and an algae waste stream and the algae drying operation may be configured to receive the algae waste stream and to produce the algae cellulose stream.

Implementations of second implementations of integrated cellulosic ethanol and biodiesel production systems may include one, all, or some of the following:

The one or more organisms may be selected from the group consisting of a fungus, a yeast, a bacterium, a protozoan, and any combination thereof.

The one or more organisms may be selected form the group consisting of *Piromyces* sp. E2, *Neocallimastix* sp. L2, *Mixotricha paradoxa, Spirochaeta endosymbiotes, Escherichia coli*, and *Escherichia coli* BL21.

The hydrolysis stage may further include one or more hydrolysis inputs including one or more compounds configured to reduce the concentration of auxin in the raw cellulose stream, assist in dehydrogenation of the raw cellulose stream, modify the pH of the raw cellulose stream, regulation the activity of the one or more organisms, or any combination thereof.

The one or more compounds may be one of capsaicin, quercetin, genestine, ethanol, and any combination thereof.

The one or more compounds may be one or more enzymes selected from the group consisting of dehydrogenase, formate, alcohol dehydrogenase E, cytosol, excrements of cephalopods or ocean mammals, and any combination thereof.

The sugars separation operation may be configured to chromatographically separate xylitol in the sugars stream to produce the xylitol stream and the separated sugars stream.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components or procedures disclosed herein. Many additional components and procedures known in the art consistent with the intended cellulosic ethanol generation systems and processes and/or assembly procedures for a cellulosic ethanol systems and processes will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such cellulosic ethanol generating systems and processes and implementing components, consistent with the intended operation.

Structure

Figure 1:
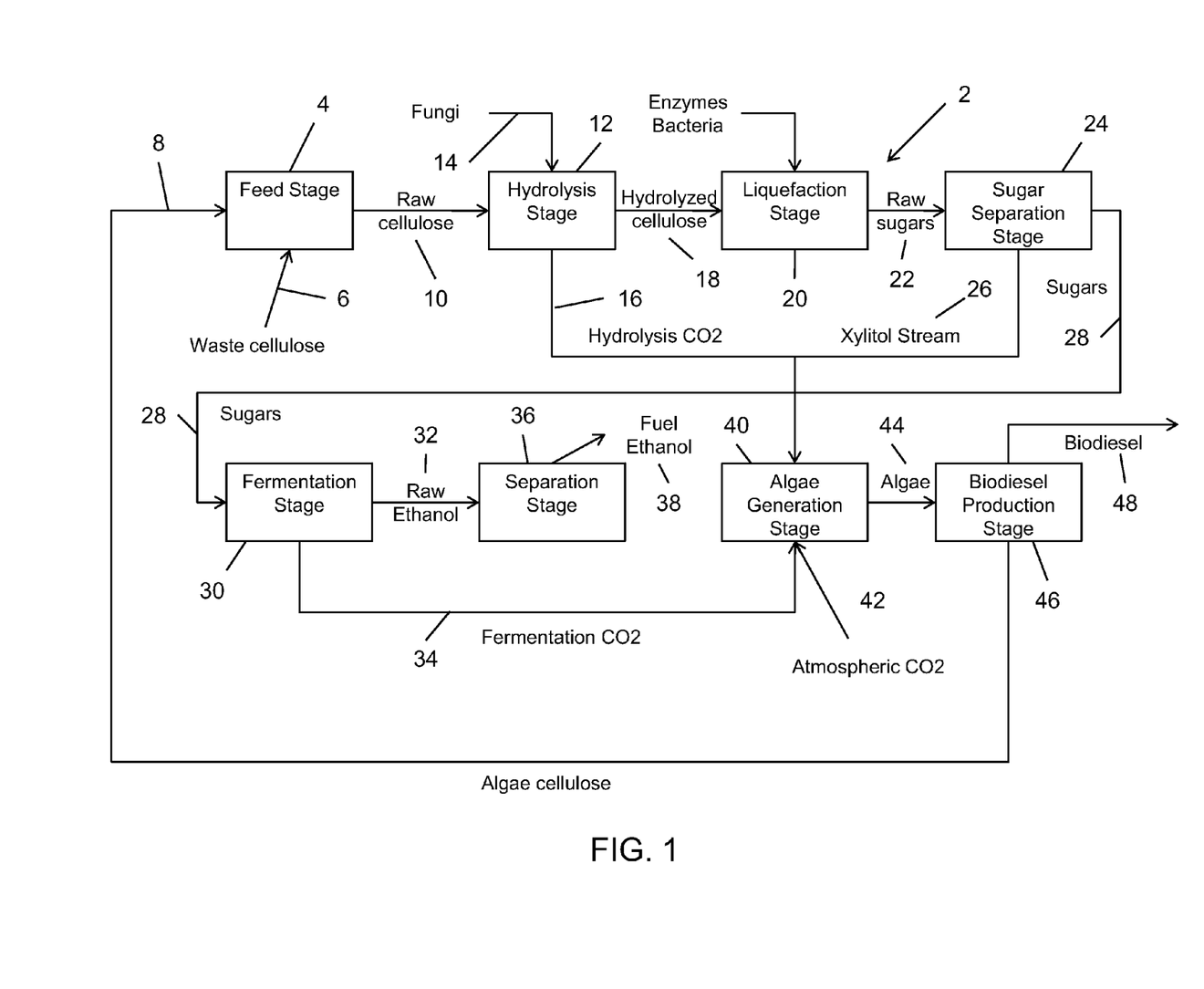
FIG. 1 is a block diagram of a first implementation of a cellulosic ethanol production system.

Referring to FIG. 1, a first implementation of a cellulosic ethanol generating system 2 is illustrated. The system includes a feed stage 4 that includes a mixing operation configured to receive a waste cellulose stream 6 of cellulosic material from biomass ground in a grinding operation. The mixing operation of the feed stage 4 mixes the cellulosic material in the waste cellulose stream 6 with cellulosic material in an algae cellulose stream 8. The cellulosic material in the waste cellulose stream 6 may be derived from any biomass source containing appreciable quantities of cellulose, such as, by non-limiting example, organic landfill waste, paper waste, paper mill process effluent, residential garbage, sawdust, and any other source of cellulosic material, including recycled cellulosic material from the cellulosic ethanol generating system 2 itself. The cellulosic material in the algae cellulose stream 8 may include any cellulosic material derived from algae including, by non-limiting example, living algae, dried algae, algae biodiesel bioreactor effluent, or any other portion of any species of algae used in an algal biodiesel process. The mixing operation of the feed stage 4 combines the cellulosic material in the waste cellulose stream 6 with that in the algae cellulose stream 8 and a certain amount of water to produce a raw cellulose stream 10.

A hydrolysis stage 12 is coupled to the feed stage 4 and is configured to receive the raw cellulose stream 10 and process it in a hydrolysis operation. The hydrolysis operation is configured to react the cellulosic material in the raw cellulose stream 10 with fungi in a fungi feed 14. The hydrolysis operation breaks down the structure of the cellulosic material in the raw cellulose stream 10 by using the fungi to attack lignins, hemicelluloses, celluloses, and cellobioses in the cellulosic material. This breakdown of the cellulosic material may allow later process steps to expose, convert, and release as much glucose and other sugar material from the cellulosic material as possible. As the fungi attack the cellulosic material, they both incorporate it into their own biomass and release free glucoses derived from the broken down lignins, hemicelluloses, celluloses, and cellobioses in the cellulosic material. The fungi may utilize any of a wide variety of enzymes and biological reaction pathways to react the cellulosic material and convert it to a food source. The particular enzymes and biological reaction pathways will depend upon the type of fungi used, the chemical makeup of the cellulosic material in the raw cellulose stream 10, and other relevant process control variables, such as, by non-limiting example, the concentration of enzymes such as alcohol dehydrogenase E, temperature, pressure, light, or any other variable capable of influencing the growth or metabolic process of the fungi or a chemical reaction occurring in the hydrolysis operation. The use of alcohol dehydrogenase E may have the effect of both enhancing and inhibiting the activity of the fungi, depending upon its concentration in the system at a given point in time. Accordingly, varying the concentration of alcohol dehydrogenase E may be used as a method of process control of the hydrolysis operation in particular implementations of cellulose ethanol production systems 2.

The enzymes and biological reaction pathways may allow glucose, ethanol, cellobiose, and other reactive enzymes to be incorporated into the raw cellulose stream 10. During the hydrolysis operation, carbon dioxide ($CO_2$) may be released by the fungi and/or the cellulosic material during the reaction period and may be captured to form a hydrolysis $CO_2$ stream 16. When ethanol is released by the fungi reacting with the cellulosic material, that ethanol may be captured and separated to form an ethanol stream for later use as fuel ethanol.

The fungi in the fungi feed 14 may include any species or combination of species from the phylum Neocallimastigomycota. In particular implementations, species selected from the genera *Neocallimastix, Piromyces*, and *Orpinomyces* may be included. For the exemplary purposes of this disclosure, specific species that may be utilized may include *Neocallimastix patriciarum, Neocallimastix patriciarum* strain 27, *Neocallimastix frontalis*, and *Piromyces* sp. strain E2. The fungi in the fungi feed 14 may be naturally occurring species or may have been created by any known type of genetic engineering, such as, by non-limiting example, breeding, recombinant DNA techniques, gene splicing, cloning, hybridization, or any other method of altering or controlling the genetic material of the fungi and/or the expression of the genetic material of the fungi. For the exemplary purposes of this disclosure, the fungi chosen are anaerobic fungi, but in other particular implementations, the fungi may be aerobic or capable of respiration by either aerobic or anaerobic pathways.

The hydrolysis operation may be carried out in any type of container, such as, by non-limiting example, a bioreactor, a vat, a tank, a plurality of bioreactors, or any other container allowing the mixing of the cellulosic material with the fungi in the fungi feed 14. The fungi feed 14 may include a wide variety of other materials intended to assist with the reaction occurring in the hydrolysis stage 12 and/or subsequent stages in the cellulosic ethanol generation process 2. These materials may include, by non-limiting example, fungi nutrients, fungi food sources, enzymes, bacteria, and any other organic or inorganic reagent, chemical or organism that may assist with hydrolysis of the cellulosic material in the raw cellulose stream 10. The fungi in the fungi feed 14 may be at least partially derived from a fungi separation operation or may be totally derived from a separate fungi growing process coupled to the fungi feed 14. The fungi in the fungi feed 14 may be grown at the same site as the cellulosic ethanol generation system 2, or may be cultivated in another location and brought in periodically or continuously as needed. The particular fungi nutrients, fungi food sources, fungi growing processes, and other chemicals used in the hydrolysis operation depend upon the particular fungus or combination of fungal species used.

For the exemplary purposes of this disclosure, the fungus included in the fungi feed 14 may be *Piromyces* sp. strain E2 and the enzymes and biological reaction pathway utilized to break down the cellulosic material in the raw cellulose stream 10 may be those described in the article by Steenbakkers et al. (hereinafter "Steenbakkers") entitled "β-Glucosidase in cellulosome of the anerobic fungus *Piromyces* sp. strain E2 is a family 3 glycoside hydrolase," Biochem. J. 370, 963-970, (2003), the disclosure of which is hereby incorporated entirely herein by reference. In addition, the fungal species, enzymes, and biological reaction pathways detailed by Boxma, et al. (hereinafter "Boxma") in the article entitled "The anaerobic chytridiomycete fungus *Piromyces* sp. E2 produces ethanol via pyruvate:formate lyase and an alcohol dehydrogenase E," Molecular Microbiology 51(5), 1389-1399 (2004), the disclosure of which is hereby incorporated entirely herein by reference, may be utilized in particular implementations. These references also disclose exemplary techniques and processes for isolating, cultivating, utilizing, growing, and analyzing fungi that may be used in particular implementations of cellulosic ethanol production systems and processes and Steenbakkers and Boxma are specifically incorporated by reference herein for their relevant teachings on these subjects.

After being processed by the fungi in the hydrolysis operation of the hydrolysis stage 12, the cellulosic material in the raw cellulose stream 10 is converted to a hydrolyzed cellulose stream 18. A liquefaction stage 20 is coupled to the hydrolysis stage 12 and is configured to receive the cellulosic material in hydrolyzed cellulose stream 18. The hydrolysis stage 12 may include a fungi separation operation, a heated sugar formation operation, and a liquefaction operation. The fungi separation operation may permit some or all of the fungi in the hydrolyzed cellulose stream 18 leaving the hydrolysis stage 12 to be separated. The separated fungi may be either partially or fully recycled back to the hydrolysis stage, may be partially or fully discarded, or may be partially or fully processed and reintroduced into the hydrolyzed cellulose stream 18 to provide additional cellulosic material for ethanol generation as a recycled fungi stream. The fungi separation operation may occur using any of many techniques known to those of skill in the art, such as, by non-limiting example, centrifugation, settling, or any other method of concentrating and removing fungi from a stream.

The heated sugar formation operation of the liquefaction stage 20 raises the temperature of the hydrolyzed cellulose stream 18 to release sugars from the cellulosic material contained in it. The heated sugar formation operation may be a simple heating step prior to introduction into further process operations or may involve maintaining the hydrolyzed cellulose stream 18 at an elevated temperature for an extended period of time. Enzymes and/or bacterial may be added to the hydrolyzed cellulose stream 18 at this point in particular implementations. For the exemplary purposes of this disclosure, the heated sugar formation operation may be conducted at 80-100 C for an hour and a half. The heated sugar formation operation may take place in any appropriate heating vessel or structure, such as, by non-limiting example, a jet cooker, a heat exchanger, a heated vessel, or any other heat transfer structure capable of raising the temperature of the hydrolyzed cellulose stream 18.

The liquefaction stage 20 may also include a liquefaction operation configured to react the cellulosic material in the hydrolyzed cellulose stream 18 with one or more enzymes and/or one or more bacteria. The liquefaction operation may take place at elevated or ambient temperatures, depending upon the requirements of the particular enzyme and/or bacterium used. The liquefaction operation may serve to further breakdown celluloses and cellobioses into glucoses and other sugars and aid in the overall conversion of the cellulosic material in the hydrolyzed cellulose stream 18 to sugars. Enzymes that may be reacted with the cellulosic material in the hydrolyzed cellulose stream include, by non-limiting example, α-amylase, β-glucanase, cellobiase, dehydrogenase, exoglucohydrolase, formate, alcohol dehydrogenase E, cytosol, pyruvate formate lyase, lignase, and excrements of cephalopods or ocean mammals. The bacteria reacted with the cellulosic material in the hydrolyzed cellulose stream may include any bacterium that is capable of releasing any of the above enzymes or any other enzyme useful in producing sugars from the cellulosic material in the hydrolyzed cellulose stream 18. In other implementations, a fungus may be added to the hydrolyzed cellulose stream to further aid in the conversion of the cellulosic material in the hydrolyzed cellulose stream 18 to sugar. The liquefaction operation, in combination with the fungi separation operation and the heated sugar formation operation, if present, may produce a sugars stream 22 and a recycled fungi stream. The sugars stream 22 may include a mixture of a number of different sugars, including glucoses and xylitol. The liquefaction operation may take place in any vessel or plurality of vessels capable of handling the cellulosic material in the hydrolyzed cellulose stream 18 and maintaining control of temperature and other relevant process variables.

A sugar separation stage 24 may be coupled to the liquefaction stage and configured to receive the sugars stream 22. The sugar separation 24 may include a sugar separation operation and a mash cooling operation. The sugar separation operation may separate fermentable sugars, such as glucoses, from non-fermentable sugars, such as xylitol, thereby helping to increase the productivity of the fermentation operation. The sugar separation operation may take place using a wide variety of techniques known in the art, including, by non-limiting example, chromatography, fractionation, or any other method of separating various sugar molecules by physical property. For the exemplary purposes of this disclosure, the sugar separation operation may occur using a strong base anion resin in a chromatography process, as described in U.S. Pat. No. 6,451,123 to Saska, et al. (hereinafter "Saska") entitled "Process for the Separation of Sugars," issued Sep. 17, 2002, the disclosure of which is hereby incorporated entirely herein by reference. When the separation operation is performed using the process disclosed in Saska, much of the xylitol in the sugars stream 22 may be separated, producing a xylitol stream and a separated sugars stream 28. Because of the separation operation, the separated sugars stream 28 may contain a substantially greater percentage of fermentable sugars than existed in the sugars stream 22.

The mash cooling operation of the sugar separation stage 24 may occur either before, as part of, or after the sugar separation operation in particular implementations. For the exemplary purposes of this disclosure, the mash cooling operation occurs after the sugar separation operation and serves to reduce the temperature of the separated sugars stream 28 in particular to a level useful for introduction into a fermentation process.

A fermentation stage 30 is coupled to the sugar separation stage 24 and configured to receive the separated sugars stream 28. The fermentation stage 30 may include a fermentation operation configured to react the separated sugars stream 28 with a yeast feed to produce a raw ethanol stream 32 and a fermentation $CO_2$ stream 34. The yeasts may consume or ferment the sugars present in the separated sugars stream 28 and release ethanol, $CO_2$ and other byproducts as a result. The released $CO_2$ may be captured to produce the fermentation $CO_2$ stream 34. The remaining liquid material may pass out of the fermentation stage 30 as the raw ethanol stream 32. The fermentation operation may take place in at least one fermenter under conditions such as, by non-limiting example, a specified period of time, a particular temperature range, in the presence of certain nutrients and any other process variable condition or component useful for the regulation of yeast growth. The yeast included in the yeast feed may be any of a wide variety of fungi and/or bacteria conventionally used to convert glucoses and other sugars to ethanol. For the exemplary purposes of this disclosure, the fungi and/or bacteria may be *Clostridium thermocellum, Piromonas communis* P, or *Zymomanas* sp. The yeasts and/or bacteria used may be either naturally occurring or the product of any form of genetic engineering, such as, by non-limiting example, breeding, recombinant DNA techniques, gene splicing, cloning, hybridization, or any other method of altering or controlling the genetic material of the fungi and/or bacteria and/or the expression of the genetic material of the fungi and or bacteria. Those of ordinary skill in the art will readily be able to select appropriate fermentation conditions, fermenters, and yeasts to produce ethanol using the principles disclosed in this document.

A separation stage 36 may be coupled to the fermentation stage 30 and be configured to receive the raw ethanol stream 32. The separation stage 36 may include a separation operation configured to separate ethanol from the raw ethanol stream 32 and produce a fuel ethanol stream 38 and a waste cellulose stream. The separation operation may include any of a wide variety of separation devices utilizing a number of conventional ethanol separation processes. Some of these may include, by non-limiting example, a molecular sieve, distillation, azeotropic distillation, centrifugation, vacuum distillation, or any other method of separating ethanol from water and/or fermentation byproducts. The waste cellulose stream consisting of cellulose-containing materials not converted to ethanol in the process may be reintroduced at the feed stage and mixed to become part of the raw cellulose stream 10 in particular implementations.

An algae generation stage 40 may be included as part of implementations of an cellulosic ethanol production system 2 and may be coupled to the system by being configured to receive the hydrolysis $CO_2$ stream 16, the fermentation $CO_2$ stream 34, an atmospheric $CO_2$ stream 42, and the xylitol stream 26. The algae generation stage 40 may include an algae generation operation that may include at least one algae bioreactor in which the hydrolysis $CO_2$ stream 16, the fermentation $CO_2$ stream 34, an atmospheric $CO_2$ stream 42, and the xylitol stream 26 are reacted with algae. As the algae feed on the $CO_2$ and xylitol contained in the streams, they multiply, and the multiplying algae may be removed from the at least one algae bioreactor as an algae stream 44.

A biodiesel production stage 46 may be coupled to the algae generation stage 40 and be configured to receive the algae stream 44. The biodiesel production stage 46 may include a biodiesel reaction operation and an algae drying operation. The biodiesel reaction operation may be configured to receive the algae stream 44 and process the algae in the stream to obtain biodiesel fuel, producing a biodiesel stream 48 and an algae waste stream. The algae drying operation may be configured to receive the algae waste stream and remove water and other liquids from the stream to produce the algae cellulose stream 8. The algae drying operation may not be included in particular implementations, meaning that the contents of the algae waste stream will pass directly to the algae cellulose stream 8 with little modification. Relevant teachings regarding algae generation and algal biodiesel generation may be found in U.S. Patent Application Publication No. 20070048859 to Sears, entitled "Closed System Bioreactor Apparatus," published Mar. 1, 2007 and in U.S. Patent Application Publication No. 20070048848 to Sears, entitled "Method, Apparatus, and System for Biodiesel Production from Algae," published Mar. 1, 2007 the disclosures of both of which are hereby incorporated entirely herein by reference. Particular implementations of biodiesel reaction operations may utilize an oil press and other components that aid in the obtaining of biodiesel precursors from the algae. Any biodiesel generated by the biodiesel production stage 46 may be directly marketed as fuel or may be used to for power generation for any of the process stages (hydrolysis, liquefaction, fermentation, etc).

Figure 2:
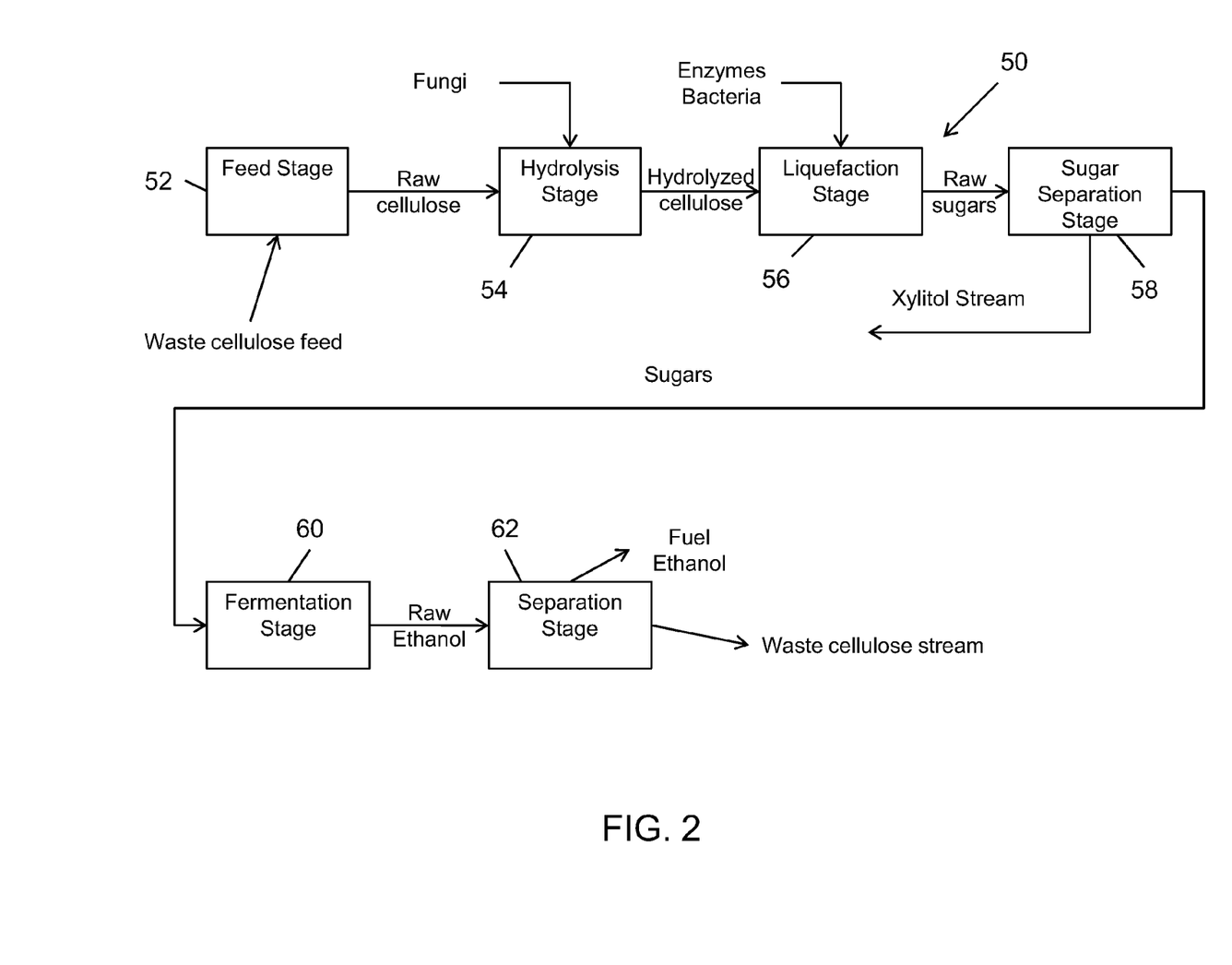
FIG. 2 is a block diagram view of a second implementation of a cellulosic ethanol production system.

Referring to FIG. 2, a second implementation of a cellulosic ethanol production system 50 is illustrated. This implementation may include a feed stage 52, hydrolysis stage 54, liquefaction stage 56, sugar separation stage 58, fermentation stage 60, and separation stage 62 that are configured like and operate similarly to those described in the implementation illustrated in FIG. 1. However, no algae generation or biodiesel production component may be included, as illustrated in FIG. 2. Accordingly, any $CO_2$ generated during the process is not recaptured to grow algae and the xylitol separated at the sugar separation stage 58 is also not used in any algae generation process. Additionally, the only biomass input to this implementation comes in the form of a waste cellulose stream 64 that does not contain any algae biomass generated as part of the cellulosic ethanol production system 50. The foregoing statement does not preclude the use of an implementation of a cellulosic ethanol production system 50 with an algal biodiesel plant, using the waste product of the algal biodiesel plant as a feed stock. However, in such implementations, the algal biodiesel plant would not be fully integrated with the cellulosic ethanol production system 50 by utilizing xylitol and/or $CO_2$ generated as a feed stock for the growth of algae.

Figure 3:
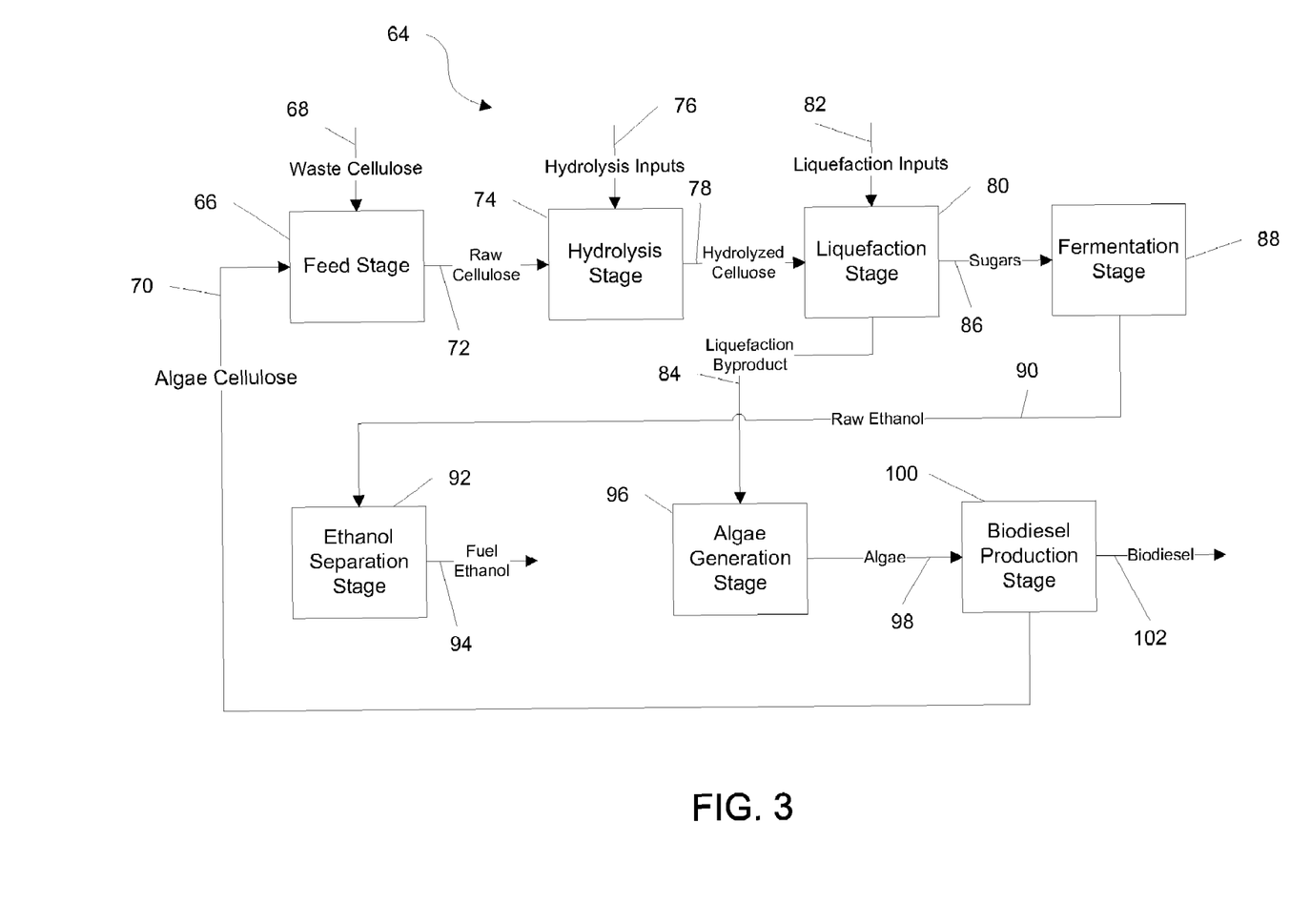
FIG. 3 is a block diagram of a third implementation of a cellulosic ethanol production system.

Referring to FIG. 3, a third implementation of a cellulosic ethanol production system 64 is illustrated. As illustrated, the system 64 includes a feed stage 66 which receives cellulose-containing material from a waste cellulose stream 68 and an algae cellulose stream 70. The feed stage 66 may operate similarly to the other feed stages in this document and produce a raw cellulose stream 72 that is then sent to a hydrolysis stage 74. As illustrated, in implementations of cellulosic ethanol production systems 64, the hydrolysis stage 74 may be configured to receive one or more hydrolysis inputs 76. The one or more hydrolysis inputs 76 may include any of a wide variety of organisms and/or chemicals that aid the process of hydrolyzing cellulose and lignin-containing materials in the raw cellulose stream 72 to form the hydrolyzed cellulose stream 78. Any of the various container types disclosed in this document may be utilized in implementations of hydrolysis stages 74.

The hydrolyzed cellulose stream 78 is received by a liquefaction stage 80, which may operate similarly to other liquefaction stages disclosed in this document. In the implementation illustrated in FIG. 3, the liquefaction stage 80 is configured to liquefy and free sugars and other fermentable materials contained in the hydrolyzed cellulose stream 78 using organisms and/or chemicals contained in one or more hydrolysis inputs 82. In particular implementations, the liquefaction stage 80 may include a heated sugar formation operation that releases additional sugars from the hydrolyzed cellulose material in the hydrolyzed cellulose stream 78 through heating the hydrolyzed cellulose stream 78. In these implementations, a mash cooling operation may also be included to reduce the temperature of the material in the stream before it is separated or fermented.

In addition, implementations of liquefaction stages 80 may be configured to separate one or more liquefaction byproducts produced during the liquefaction process to form one or more liquefaction byproduct streams 84 and a sugars stream or formed sugars stream 86. The one or more liquefaction byproduct streams 84 may include any of a wide variety of potential liquefaction byproducts, including, by non-limiting example, cellulose-containing materials, xylose-containing materials, lignin-containing materials, xylitol, organisms, enzymes, ethanol, or any other byproduct of the hydrolysis process. In implementations of cellulosic ethanol production systems where ethanol is one of the liquefaction byproducts or a byproduct of the hydrolysis stage 74 itself, the ethanol may be transported to an ethanol separation stage 92 in a hydrolysis ethanol stream. The liquefaction stage 80 may include an organisms separation operation that may allow organisms in the hydrolyzed cellulose stream 78 to be recovered and collected or recycled back to the hydrolysis stage 74 in one or more organism recycle streams. As illustrated, the sugars stream or formed sugars stream 86 is sent to a fermentation stage 88, which may operate similarly to the other fermentation stages disclosed in this document to produce a raw ethanol stream 90 and other byproduct streams, such as a fermentation $CO_2$ stream.

The raw ethanol stream 90 is then sent to an ethanol separation stage 92 which may operate similarly to other ethanol separation stages disclosed in this document to separate ethanol in the raw ethanol stream 90 from to produce a fuel ethanol stream 94.

As illustrated in FIG. 3, particular implementations of cellulosic ethanol production systems 64 may include an algae generation stage 96 coupled with the liquefaction stage 84 through one or more of the liquefaction byproduct streams 84. The algae generation stage 96 may operate similarly to other algae generation stages disclosed in this document and may contain various types of algae configured to use any of the liquefaction byproducts in the one or more liquefaction byproduct streams 84 as part of the algae's metabolic, growth, or chemical production processes. Examples of liquefaction byproducts utilized by algae in the algae generation previously discussed in this document include hydrolysis $CO_2$ and xylitol. Other liquefaction byproducts may be utilized by the algae for any of a wide variety of purposes, such as, by non-limiting example, nutrition, substrate, metabolism, chemical production, growth, or any other purpose consistent with use of the algae for biodiesel or other algal chemical production process. The algae generation stage 96 may also be configured to receive and utilize various $CO_2$ streams like those previously disclosed in this document, such as a fermentation $CO_2$ stream and an atmospheric $CO_2$ stream.

As illustrated, the algae generation stage 96 is configured to produce an algae stream 98 which is then sent to a biodiesel production stage 100. The biodiesel production stage 100 may operate similarly to the other biodiesel production stages disclosed in this document and produce a biodiesel stream 102 and the algae cellulose stream 70. As illustrated in FIG. 3, in particular implementations, the algae cellulose stream 70 may be recycled to the feed stage 66 for mixing to produce the raw cellulose stream 72. In other implementations, the algae cellulose stream 70 may not be recycled and may be used for other purposes including disposal.

A wide variety of organisms and/or chemicals may be included in the one or more hydrolysis inputs 76 in particular implementations of cellulosic ethanol production systems 64. In addition, in particular implementations, the hydrolysis stage 74 may be divided into one or more additional stages, each stage receiving one or more hydrolysis inputs different from the other stages and each stage separated by an intermediate processing operation, such as an acid neutralization, biocidal, or separation operation. The particular organisms chosen and chemicals added may perform more than one function within the hydrolysis process. For example, capsaicin may be included in the one or more hydrolysis inputs 76 to react directly with the cellulosic material in the raw cellulose stream 72, reduce the concentration of the plant hormone auxin in the cell walls of the cellulosic material in the raw cellulose stream 72, adjust the pH of the raw cellulose stream 72, and/or serve generally as an organic transport inhibitor. The foregoing example indicates that while particular chemicals and organisms may be described in this document as performing a particular function in the hydrolysis or liquefaction process in this document, the same chemicals and/or organisms may also simultaneously perform other functions in the chemical process.

In particular implementations, capsaicin, quercetin, genestine, ethanol, or any combination of these chemicals may be included in the one or more hydrolysis inputs 76. These chemicals may be used to react directly with the cellulosic material in the raw cellulose stream to perform any of a wide variety of functions, including, by non-limiting example, freeing of sugars, tissue softening, or acting as a biocide, or any other function created through direct reaction with the cellulosic material. In particular implementations, various enzymes may be reacted directly with the cellulosic material in the raw cellulose stream to aid in material breakdown through any of a variety of pathways, including, by non-limiting example, delignification, cellulosic polymer chain breakdown, fiber softening, and any other material breakdown process. The enzymes used by include, by non-limiting example, dehydrogenase, formate, alcohol dehydrogenase E, cytosol, and excrements of cephalopods or ocean mammals. Implementations may also include capsaicin, quercetin, genestine, ethanol, or any combination thereof as organic transport inhibitors to reduce the concentration of plant hormone auxin in the cell walls of the cellulosic material in the raw cellulose stream 72. Without being bound by any theory, when the concentration of auxin in the cell walls of the cellulosic material is reduced, the cell walls soften, allowing the cellulose, lignocellulose, cellobiose, and other sugar-containing materials to be made more accessible to other steps in the hydrolysis process or the liquefaction process (including the action of various organisms), thus increasing the amount of sugars produced from the cellulosic material.

In implementations of cellulosic ethanol production systems 64, capsaicin, an inorganic acid, or an organic acid, or any combination thereof may be included in the one or more hydrolysis inputs 76. Without being bound by any theory, these chemicals modify the pH of the raw cellulose stream 72 and permit greater amounts of sugars to be freed from the cellulosic material contained in the raw cellulose stream 72. Any of a wide variety of inorganic acids may be utilized, such as, by non-limiting example, sulfuric, nitric, phosphoric, or any other electron acceptor including an inorganic component. A wide variety of organic acids may be utilized in particular implementations as well, including, by non-limiting example, acetic acid, citric acid, carboxylic acids, and any other electron acceptor including an organic component. The one or more hydrolysis inputs 76 may include a pH modifying chemical particularly in those implementations of cellulosic ethanol production systems 64 that do not use organisms as part of the hydrolysis process. In these implementations, the hydrolysis of the cellulosic material occurs primarily by chemical action alone, without involving the any organism.

In implementations of cellulosic ethanol production systems performing hydrolysis by chemical action alone and through organisms, various dehydrogenating chemicals may be included in the one or more hydrolysis inputs 76. Without being bound by any theory, these dehydrogenating chemicals, such as enzymes or organic transport inhibitors, may serve to remove hydrogen from the cellulosic material in the raw cellulose stream and make it more susceptible to chemical attack/reaction and/or organism metabolism, thus increasing the amount of sugars released during the hydrolysis process or made available for release during the liquefaction process. The enzymes used may include, by non-limiting example, dehydrogenase, formate, alcohol dehydrogenase E, cytosol, and excrements of cephalopods or ocean mammals, any combination thereof, or any other dehydrogenating compound operating in a catalytic manner. The one or more organic transport inhibitors utilized may include capsaicin, quercetin, genestine, ethanol, or any other transport inhibitor.

In implementations of cellulosic ethanol production systems 64 utilizing organisms in the hydrolysis step, the characteristics of the hydrolysis process may be regulated using a chemical that regulates the activity of the organisms as one of the hydrolysis inputs 76. The chemicals may include one or more enzymes, such as, by non-limiting example, dehydrogenase, formate, alcohol dehydrogenase E, cytosol, and excrements of cephalopods or ocean mammals. Without being bound by any theory, the chemical may participate in the metabolic cycle utilized by the particular organism being used for the hydrolysis process. For example, while alcohol dehydrogenase E is not generally considered a cellulase, since it is involved in the cellulose metabolic pathway of *Piromyces* sp. E2, addition of the enzyme will serve to govern the activity of the fungus in the hydrolysis stage.

A wide variety of organisms can be used in implementations of cellulosic ethanol production systems 64 in both the hydrolysis stage 74 and in the liquefaction stage 82. For example, a fungus, yeast, bacterium, protozoan or any combination thereof may serve both to hydrolyze and/or to assist with the liquefaction of the cellulosic material being processed. Xylophageous organisms may be particularly useful, since they can work to produce pentoses alongside other organisms that focus on breaking down cellulose into hexoses and increase the total sugars produced in the hydrolysis stage 74 and/or the liquefaction stage 82. For the exemplary purposes of this disclosure, *Piromyces* sp. E2, *Neocallimastix* sp. L2, *Mixotricha paradoxa*, *Spirochaeta endosymbiotes*, *Escherichia coli*, and *Escherichia coli* BL21, and any combination thereof may all be employed in the hydrolysis stage 74. In addition, *Escherichia coli* and any of many variants may also be employed in the fermentation stage 88 to form ethanol.

A wide variety of other chemicals may be introduced as one of the one or more hydrolysis inputs 76. For example, xylitol produced in the liquefaction stage 82 may be introduced as one of the one or more hydrolysis inputs 76 when organisms capable of metabolizing the xylitol and/or converting it to fermentable material are contained in the hydrolysis stage 74. In these implementations, the reintroduction of the xylitol may allow for increasing the biomass in the hydrolysis stage 74. In addition, in other particular implementations, any other separated waste sugars produced and/or separated in the liquefaction stage 82 may be reintroduced into the hydrolysis stage 74 and any fermentable portions continued through the process to the fermentation stage 88.

In implementations of cellulosic ethanol production systems 2, 50, and 64, a wide variety of fermentation stage designs are possible including both continuous, semi-continuous, and batch fermentation stage designs. In systems employing semi-continuous or batch fermentation stage designs, a replication or holding tank may need to be employed as part of the hydrolysis stage to allow replication of organisms, or holding of processed hydrolyzed material while the fermentation stage is in operation. Many other fermentation stage and hydrolysis stage designs are possible depending upon a wide variety of factors, including, by non-limiting example, organism type, neutralization requirements, feedstock material, capital cost, operating expenses, and any other variable with potential process impact.

Use

Implementations of cellulosic ethanol production systems 2, 50, 64 may utilize implementations of cellulosic ethanol production processes. These processes may include various process steps corresponding with various stages and operations within the cellulosic ethanol production systems 2, 50, 64. Accordingly, implementations of cellulosic ethanol production systems 2, 50, 64 may perform operations such as providing, hydrolyzing, liquefying, separating, fermenting, generating, and reacting, as well as many other functions inherent in the operation of implementations of cellulosic ethanol production systems 2, 50, 64. These cellulosic ethanol production processes may utilize the same fungi, enzymes, and bacteria previously disclosed while performing the various process steps.

For the exemplary purposes of this disclosure, a particular implementation of a cellulosic ethanol production process 2 includes providing a raw cellulose stream 10 by mixing a waste cellulose stream 4 and an algae cellulose stream 8 and hydrolyzing the raw cellulose stream 10 to form a hydrolyzed cellulose stream 18, a hydrolysis $CO_2$ stream 16, and an ethanol stream by reacting the raw cellulose stream 10 with one or more fungi selected from the group consisting of the genera *Neocallimastix, Piromyces*, and *Orpinomyces* in a fungi feed 14. Any of the other organisms described in this document could be similarly employed. In particular implementations, however, no organisms may be used, and the hydrolysis step may be accomplished purely through chemical treatment. The implementation includes liquefying the hydrolyzed cellulose stream 18 to produce a sugars stream 22 by heating the hydrolyzed cellulose stream 18 and by reacting the hydrolyzed cellulose stream 18 with one or more enzymes, one or more bacteria, or with one or more enzymes in combination with one or more bacteria. The implementation also includes separating the sugars in the sugars stream 22 to produce a xylitol stream 26 and a separated sugars stream 28, fermenting the separated sugars stream 28 to produce a raw ethanol stream 32 and a fermentation $CO_2$ stream 34 by reacting the separated sugars stream 28 with a yeast feed in at least one fermenter, separating the raw ethanol stream 32 to produce a fuel ethanol stream 38 and a waste cellulose stream. The implementation may also include generating an algae stream 44 by reacting the hydrolysis $CO_2$ stream 16, the fermentation $CO_2$ stream 34, an atmospheric $CO_2$ stream 42, and the xylitol stream 26 with algae in at least one algae bioreactor and reacting the algae stream 44 in the at least one biodiesel reactor producing an algae cellulose stream 8 and a biodiesel stream 48.

For implementations of cellulosic ethanol production systems 50, the process steps of generating the algae stream and reacting the algae stream to produce a biodiesel stream and an algae cellulose stream would be absent.

Testing

A paper experiment was performed using *Piromyces* sp. E2 to determine an exemplary amount of fungi organelles required per ton of biomass as a function of the potential percentage of available sugar in the biomass varied. The results of the paper experiment were used to determine an equation for the number of organelles per ton of biomass. The paper experimental results are listed below in Table 1. Similar paper experimental results were observed for a combination of *Neocallimastix* sp. L2 and *E. coli*.

TABLE 1

| | Actual Incubation of *Piromyces* sp. E2 (in 0.005 gallons) & Growth (Lbs of wt) | | | | |
|---|---|---|---|---|---|
| Organelles | Sugar Solution | Hydrogen | Ethanol | | Biomass Remain |
| 1.77 | 30.00% | 0.00002 | 0.00005 | wgt/vol | 2.06 |
| 1.97 | 35.00% | 0.00002 | 0.00006 | wgt/vol | 2.30 |

TABLE 1-continued

| | Actual Incubation of *Piromyces* sp. E2 (in 0.005 gallons) & Growth (Lbs of wt) | | | | |
|---|---|---|---|---|---|
| Organelles | Sugar Solution | Hydrogen | Ethanol | | Biomass Remain |
| 2.81 | 40.00% | 0.00003 | 0.00008 | wgt/vol | 3.28 |
| 3.82 | 45.00% | 0.00003 | 0.00011 | wgt/vol | 4.45 |
| 5.63 | 50.00% | 0.00005 | 0.00016 | wgt/vol | 6.56 |
| 7.64 | 55.00% | 0.00007 | 0.00022 | wgt/vol | 8.91 |
| 9.65 | 60.00% | 0.00009 | 0.00027 | wgt/vol | 11.25 |
| 11.66 | 65.00% | 0.00011 | 0.00033 | wgt/vol | 13.59 |

The resulting equation was $y=0.00067x+29.07847$ where y is the number of organelles per ton of biomass and x is the percentage of available sugar in the biomass.

In places where the description above refers to particular implementations of cellulosic ethanol production systems and processes, it should be readily apparent that a number of modifications may be made without departing from the spirit thereof and that these implementations may be applied to other cellulosic ethanol production systems and processes.

The invention claimed is:

1. An integrated cellulosic ethanol and biodiesel production system comprising:

a feed stage that receives a waste cellulose stream and an algae cellulose stream, and produces a raw cellulose stream from the combination thereof;

a hydrolysis stage coupled with the feed stage that hydrolyzes the raw cellulose stream from the feed stage to produce a hydrolyzed cellulose stream wherein the hydrolysis stage further comprises one or more hydrolysis inputs and wherein the one or more hydrolysis inputs comprise one or more compounds to;

reduce the concentration of auxin in the row cellulose stream;

assist in dehydrogenation of the raw cellulose stream;

modify the pH of the raw cellulose stream;

or any combination thereof;

a liquefaction stage coupled with the hydrolysis stage that liquefies the hydrolyzed cellulose stream from the hydrolysis stage to produce a formed sugars stream and one or more liquefaction byproduct streams;

a fermentation stage coupled with the liquefaction stage wherein the formed sugars stream from the liquefaction stage is reacted with a yeast feed in at least one fermenter to produce a raw ethanol stream;

a separation stage coupled with the fermentation stage that separates ethanol from the raw ethanol stream from the fermentation stage to produce a fuel ethanol stream;

an algae generation stage also coupled to the liquefaction stage comprising at least one algae bioreactor wherein the one or more liquefaction byproduct streams are reacted with algae in the at least one algae bioreactor to produce an algae stream;

a biodiesel production stage coupled with the algae generation stage that produces from the algae stream of the algae generation stage a biodiesel stream using a transesterification process, and an algae cellulose stream, wherein the algae cellulose stream is coupled to the feed stage.

2. The system of claim 1, wherein the one or more hydrolysis input compounds is one of capsaicin, quercetin, genistien, ethanol, and any combination thereof.

3. The system of claim 1, wherein additionally the one or more hydrolysis input compounds is one or more enzymes selected from the group consisting of dehydrogenase, alcohol dehydrogenase E, and any combination thereof.

4. The system of claim 1, wherein one of the one or more liquefaction byproduct streams includes xylitol.

* * * * *